United States Patent [19]

Tricaud et al.

[11] Patent Number: 5,612,022

[45] Date of Patent: Mar. 18, 1997

[54] PULVERULENT HAIR BLEACH OF PEROXYGEN OXIDIZER AND POLYOXYETHYLENE/POLYOXY PROPYLENE COPOLYMER

[75] Inventors: Caroline Tricaud, Cormeilles En Parisis; Jean-Marie Millequant, Saint-Maur; Henri Sebag, Paris, all of France

[73] Assignee: L'Oreal, Paris, France

[21] Appl. No.: 683,104

[22] Filed: Jul. 16, 1996

Related U.S. Application Data

[60] Continuation of Ser. No. 475,649, Jun. 7, 1995, abandoned, which is a division of Ser. No. 361,659, Dec. 22, 1994, abandoned.

[30] Foreign Application Priority Data

Jan. 14, 1994 [FR] France .................. 94 00366

[51] Int. Cl.$^6$ .................. A61K 7/07; A61K 7/135
[52] U.S. Cl. .................. 424/62; 424/401; 424/501
[58] Field of Search .................. 424/62, DIG. 3, 424/401, 501

[56] References Cited

U.S. PATENT DOCUMENTS

| | | | |
|---|---|---|---|
| 3,639,574 | 2/1972 | Schmolka | 424/68 |
| 3,852,210 | 12/1974 | Krezanoski | 252/95 |
| 4,107,065 | 8/1978 | Gray | 252/99 |
| 4,170,637 | 10/1979 | Pum | 424/62 |
| 4,327,751 | 5/1982 | Evans | 424/62 |
| 5,279,313 | 1/1994 | Clausen et al. | 424/62 |
| 5,294,436 | 3/1994 | Cope et al. | 424/62 |

FOREIGN PATENT DOCUMENTS

| | | |
|---|---|---|
| 0560088 | 9/1993 | European Pat. Off. . |
| 0574696 | 12/1993 | European Pat. Off. . |
| 2276809 | 1/1976 | France . |
| 3434468 | 3/1986 | Germany . |
| 2033939 | 5/1980 | United Kingdom ....... 424/62 |

OTHER PUBLICATIONS

Derwent accession No. 93–289629/37 for European Application No. 560,088, Goldwell AG, Sep. 1993.
Derwent Abstract No. 001572324 of French Pat. App. FR–A–2276809, Jan. 30, 1976.
Derwent Abstract No. 004585337 of German Pat. App. DE–A–3434468, Mar. 27, 1986.
Derwent Abstract No. 009596082 of European Pat. App. EP–A–0560088, Sep. 15, 1993.
Derwent Abstract No. 009713558 of European Pat. App. EP–A–0574696, Dec. 22, 1993.

*Primary Examiner*—Robert E. Sellers
*Attorney, Agent, or Firm*—Finnegan, Henderson, Farabow, Garrett & Dunner, L.L.P.

[57] ABSTRACT

A process for preparing a pulverulent, anhydrous hair bleaching composition comprises mixing in a non-solvent medium at room temperature a dry bleaching powder of a peroxygen compound oxidizing agent and at least one anhydrous block and/or random polyoxyethylene/polyoxypropylene copolymer which is liquid and water-soluble at room temperature.

1 Claim, No Drawings

PULVERULENT HAIR BLEACH OF PEROXYGEN OXIDIZER AND POLYOXYETHYLENE/POLYOXYPROPYLENE COPOLYMER

This is a continuation application of pending prior application Ser. No. 08/475,649, filed Jun. 7, 1995, which is a divisional appln. Ser. No. 08/361,659 filed Dec. 22, 1994, all now abandoned.

The present invention relates to cosmetic compositions for bleaching the hair having improved properties. More particularly, it relates to bleaching compositions in the form of fine, anhydrous, free-flowing, homogeneous and non-dusty powders.

It is known to bleach hair using pastes (or cataplasms) which are applied directly to the hair and which are obtained by mixing, at the time of use, a bleaching composition based on peroxygen compounds, which as defined herein are those compounds which yield hydrogen peroxide in aqueous media (oxidizing agents), with water, or most often with hydrogen peroxide. The bleaching composition consists, in a known manner, of a peroxygen compound (essential component), generally a sodium, potassium or ammonium persulphate or perborate, and sometimes a percarboxylic acid salt or a peroxide, for example, a barium, strontium, urea, or melamine peroxide. Most often, these compositions contain, in addition, in a known manner, highly alkaline agents such as alkali or alkaline-earth metasilicates, phosphates or carbonates (pH regulators). Finally, they may moreover optionally contain other additives or adjuvants conventionally used in the field: agents for controlling the release of oxygen during the mixing with hydrogen peroxide, such as magnesium carbonate or magnesia; thickeners such as cellulose derivatives (carboxymethylcellulose, for example) or starch and its derivatives, or alternatively guar and xanthan gums and alginates; surfactants, in particular anionic (especially alkyl sulphates); dyes; sequestrants; perfumes. Such bleaching compositions are described, for example, in "The Science of Hair Care" by C. ZVIAK, Marcel Decker Inc. 1986, pp. 225–226, the entire disclosure of which pages is hereby incorporated by reference.

The hair bleaching compositions most widely used up until now are in the form of powders (mixtures) of small particle size, i.e., particles whose size is generally less than a millimeter, preferably less than a few hundred microns, which allows easy and rapid dissolution and/or dispersion in hydrogen peroxide. However, such pulverulent compositions, given the finely divided state in which they exist, have several disadvantages: they are highly volatile and thus emit, during their handling, harmful dusts containing peroxygen compounds and highly irritating to the lungs; these powders are moreover delicate not only to handle but also to measure out, presenting dusting and castability problems.

In order to try to solve the above-mentioned problems, a hair bleaching powder completely free of dust (or fines) and obtained by adding an oil or a liquid wax to the initial mixture of powders (solid peroxide +solid carrier based on alkali metal salts and various adjuvants described above) is described in European Patent Application EP-A 0,560,088. However, the bleaching powder described in EP-A-0,560, 088, although effectively denser and less dusty than conventional bleaching powders, happens to have other disadvantages, in particular due to the presence of the oil or the wax, which can substantially limit the benefit of its use. Thus, with this powder, it is observed that the mixtures with hydrogen peroxide take a long time to prepare and give brilliant cataplasms with an oil appearance; that a thorough removal of the product from the hair takes a long time and is tedious; that the shampoos used to facilitate this removal after the bleachings no longer foam; and that finally, after the bleaching operation, the hair retains an unpleasant greasy and heavy feel.

Following major research studies on this subject, it has been found by the inventors that it is possible to obtain, in the form of powders, bleaching cosmetic compositions for the hair not having any of the above-mentioned undesirable effects linked to the prior art compositions, by introducing a specific polymer into said compositions. This discovery forms the basis of the present invention.

Thus, according to the present invention, there are now proposed new cosmetic compositions for bleaching hair, comprising at least one oxidizing agent selected from peroxygen compounds and at least one block and/or random linear polyoxyethylene/polyoxypropylene copolymer, the copolymer being anhydrous and, at room temperature, further being both liquid and soluble in water, and the composition also being pulverulent and anhydrous.

The process for synthesizing the bleaching powders according to the invention, itself constituting a second subject of the present invention, comprises mixing, in non-solvent medium and at room temperature, a dry bleaching powder based on solid peroxygen compounds, with a copolymer as defined above. According to the invention, bleaching compositions are thus obtained which are in the form of fine but nevertheless dense and nonvolatile powders (absence of dusting). They are, in addition, anhydrous and flow well (low caking; increased ease of measuring out). Moreover, their mixing with hydrogen peroxide can be rapid and easy and results in very homogeneous pastes. The mixtures obtained can be unctuous, creamy, lump-free and have a much more pleasant appearance than that obtained with powders treated with inorganic oils such as silicone oils or paraffin oils, or waxes. In addition, the application of the cataplasms can be easy and they can adhere well to the hair and not slip. Finally, their removal is distinctly better than in the case of powders with oil or with wax; the shampoos foam, and the hair is not greasy, remains shiny and retains a natural feel.

Other characteristics, aspects and advantages of the invention will emerge even more clearly on reading the following description, as well as various concrete examples, which are not at all limiting, but intended to illustrate the invention.

The copolymers used within the framework of the present invention are products which are already well-known per se and which can be easily synthesized by a person skilled in the art. They are moreover available commercially. As indicated earlier, they belong to the general family of block linear polyoxyethylene/polyoxypropylene copolymers.

In a known manner, the products in accordance with the invention can thus be represented by the following formulae (1) or (2):

$(AO)_x(EO)_m(AO)_y$ (1) or
$(AO)_x(PO)_m(AO)_y$ (2)

in which EO designates a unit which is derived from ethylene oxide, PO a unit which is derived from propylene oxide, AO one of the EO or PO units as defined above, the terminal units of the polymeric chain being hydroxyl functional groups or $C_1$–$C_2$ alkoxy functional groups (i.e., oxymethyl or oxyethyl), at least one of these terminal units being necessarily a hydroxyl functional group, and the subscripts x, y and m being integers such that the said copolymer is, at room temperature, liquid on the one hand and soluble in water on the other.

These polyoxyethylene/polyoxypropylene block copolymers may be conventionally prepared, according to the cases, (i) by reacting a polyoxypropylene glycol (difunctional) with either ethylene oxide alone, which results in the production of linear block copolymer of formula $(AO)_x(PO)_m(EO)_y$, or with an ethylene oxide propylene oxide mixture, which results in the production of a linear random copolymer of formula $(AO)_x(PO)_m(AO)_y$; or (ii) by reacting a polyoxyethylene glycol (difunctional) with either propylene oxide alone, which results in the production of a linear block copolymer of formula $(PO)_x(EO)_m(PO)_y$, or with a propylene oxide/ethylene oxide mixture, which results in the production of a linear random copolymer of formula $(AO)_x(EO)_m(AO)_y$. In the cases where it is desired to use copolymers containing at one of their ends a $C_1$–$C_2$ alkoxy group, they can be obtained by block and/or random polyaddition of ethylene oxide and propylene oxide to a $C_1$–$C_2$ alcohol (i.e. methanol or ethanol). Depending on the selected proportions between the various reagents used in the above reactions, it is possible, inker alia, to adjust the physical state (solid/liquid), the viscosity and the solubility, in water, of the copolymers obtained. Such products are especially sold under the general trade name PLURONICS® by the companies WYANDOTTE and BASF, or under the name SYNPERONIC® by the company ICI.

According to an important characteristic of the present invention, there is selected among the above copolymers only those which are (i) anhydrous, (ii) liquid at room temperature and (iii) soluble in water at room temperature. By room temperature, there is understood herein a temperature which may range from about 15° C. to 30° C. Moreover, by liquid, there is understood more particularly a product whose viscosity is less than 1000 centipoises, preferably less than 100 centipoises. By anhydrous, it is understood that the water content of the product is less than 1% by weight, preferably less than 0.5% by weight. Finally, by soluble in water, there is intended more particularly a polymeric product whose solubility in water is at least 1 g/l, preferably at least 10 g/l.

According to the present invention, it is of course possible to use one or more of the copolymers as defined above.

The copolymers preferred within the framework of the present invention are the linear block copolymers of the $(EO)_x(PO)_m(EO)_y$ type.

The proportion of copolymer(s) in the bleaching compositions according to the invention generally ranges from 5 to 27% by weight relative to the total weight of the said composition. Preferably, this content ranges from 5% to less than 25% by weight.

The other essential constituent, i.e., at least one peroxygen compound as an oxidant, or optional constituents, such as pH regulators, thickeners, cosmetic additives and the like, which are used or which can be used in the composition of the products according to the invention are those which are usually encountered for hair bleaching compositions, especially those indicated in the introductory part of the present description, and which are entirely suitable here.

As a guide, the hair bleaching formulations in accordance with the invention generally have the following compositions:

oxidizing agent(s) (preferably chosen from alkali metal persulphates): from 20 to 60% by weight, preferably from 30 to 50% by weight, relative to the whole formulation;
copolymer(s): as indicated above;
pH regulator(s) (preferably chosen from alkali metal metasilicates): from 5 to 15% by weight, preferably from 9 to 14% by weight, relative to the whole formulation;
thickener(s): from 0.5 to 5% by weight, preferably from 1 to 3% by weight, relative to the whole composition;
optional cosmetic adjuvant(s): qs 100% by weight.

As indicated above, the bleaching compositions according to the invention are provided in a pulverulent solid state. The particles constituting this powder have a size generally less than 1000 microns (1 mm) but in particular have a particle size distribution such that the quantity by weight of the particles which have a size less than or equal to 65 microns (quantity of fines) is remarkably low. Thus, this quantity of fines is generally less than or equal to 5% by weight, preferably less than 2% by weight, and still more preferably less than 1% by weight. This characteristic makes the powders according to the invention non-dusty. The maximum particle size indicated above makes, for its part, mixtures with hydrogen peroxide much easier to produce.

According to a first embodiment of the process for synthesizing the bleaching compositions according to the invention, conventional dry bleaching powders based on peroxygen compounds (i.e., powders which it is desired in particular to make nonvolatile) are introduced into a mechanical mixer (mixer of the LODIGE or WINKWORTH type in particular); these powders are then stirred, then the Copolymer(s) in accordance with the invention is(are) incorporated into them and the whole is mixed, still by mechanical stirring, for homogenization, and finally the resulting product which constitutes the composition according to the invention is recovered.

According to another embodiment, the liquid copolymer(s) in accordance with the invention is (are) simply sprayed, e.g., by atomization, onto the initial bleaching powders maintained in a stirred condition, e.g., by mechanical stirring or by fluidized bed. The resulting product which constitutes the composition according to the invention is then recovered.

The above two embodiments are achieved at room temperature and without using third solvents, such as water or organic solvents (dry mixture), even at the copolymer introducing stage. The proportions of initial powder to copolymer(s) are chosen in the same manner as indicated above for the final compositions desired. In both cases, the mixing times make it possible to control the final particle sizes.

The pulverulent bleaching compositions in accordance with the invention can then be used on the hair in the conventional manner and in a manner known per se in the hair bleaching field. Thus, the bleaching compositions are preferably mixed in the form of powders with a hydrogen peroxide solution at about 6–12% by volume, preferably at about 9% by volume, and this in a ratio generally of the order of 1:1, then the mixing is performed until a homogeneous paste is obtained which is then applied to the hair and which is allowed to act for a period of between about 25 and 45 minutes. The compositions is then removed from the hair, e.g., by rinsing with water and/or shampoos.

Concrete examples illustrating the invention will now be given. It is to be understood that such examples are not limiting, but merely illustrative.

EXAMPLE 1

A bleaching composition in accordance with the invention was prepared (Composition 1) which had the following composition (% by weight):

| | |
|---|---|
| Potassium persulphate | 25% |
| Ammonium persulphate | 25% |
| Sodium metasilicate | 10% |
| Ammonium chloride | 5% |
| Sequestrant | 2% |
| Silica | 13% |
| Copolymer 1[(1)] | 20% |

[(1)]: copolymer of the 8EO/30PO/8EO type sold under the name SYNPERONIC PE/L62 by the company ICI.

The procedure was the following: the various solid compounds constituting the initial bleaching powder (i.e. not containing the copolymer) were introduced into a LODIGE type mixer, they were dry-mixed for 20 minutes in the mixer, then the copolymer serving as coating agent was introduced into the latter and the whole was mixed (still dry) for homogenization for 20 minutes.

The particle size of the final bleaching powder obtained (determined by sieving) is indicated in the table given below (Composition 1). This table indicates the % by weight of the particles present in the composition whose size is within a given size range.

As a comparison, the particle size of the bleaching powder before the introduction of the copolymer (Composition 0) is also indicated in the table.

EXAMPLE 2

By repeating the procedure described in Example 1, a second composition in accordance with the invention (Composition 2) similar to that of Example 1 was prepared, the only difference being that the copolymer 1 was replaced here with a copolymer of the 6EO/19PO/6EO type sold under the trade name PLURONIC PE 4300 by the company BASF.

The particle size of the final bleaching powder obtained determined by sieving) is indicated in the table given below (Composition 2).

EXAMPLE 3

By repeating the procedure of Example 1, a third composition in accordance with the invention (Composition 3) having this time the following composition by weight was prepared:

| | |
|---|---|
| Potassium persulphate | 60% |
| Ammonium persulphate | 20% |
| Sodium metasilicate | 10% |
| Ammonium chloride | 5% |
| Copolymer 1[(1)] | 5% |

[(1)]: copolymer of the 8EO/30PO/8EO type sold under the name SYNPERONIC PE/L62 by the company ICI.

The particle size of the final bleaching powder obtained (determined by sieving) is indicated in the table given below (Composition 3).

The particle size of the powder mixture before the introduction of the copolymer was identical to that of the Composition 0 of Example 1.

The three Compositions 1, 2 and 3 were completely dust-free.

TABLE

| Size$\Phi$ (μm) | Composition 0 | Composition 1 | Composition 2 | Composition 3 |
|---|---|---|---|---|
| $\Phi > 710$ | 2.2 | 30.24 | 29.02 | 32.00 |
| $355 < \Phi < 710$ | 7.8 | 31.64 | 27.96 | 50.60 |
| $100 < \Phi 355$ | 28.46 | 21.56 | 21.60 | 13.11 |
| $63 < \Phi < 100$ | 52.86 | 15.94 | 19.68 | 3.26 |
| $0 < \Phi < 63$ | 7.74 | 0.20 | 0.40 | 0.00 |

What is claimed is:

1. A process for preparing a cosmetic composition for bleaching hair, wherein said composition consists essentially of at least one oxidizing agent selected from peroxygen compounds and from 5 to 27% by weight relative to the total weight of said composition of at least one block and/or random linear polyoxyethylene/polyoxypropylene copolymer, said copolymer being anhydrous and, at room temperature, further being both liquid and soluble in water and said composition being pulverulent and anhydrous, the process comprising the step of mixing, in non-solvent medium and at room temperature, a dry bleaching powder based on solid peroxygen compounds, with said copolymer.

* * * * *